US011885789B2

(12) United States Patent
Borgman et al.

(10) Patent No.: US 11,885,789 B2
(45) Date of Patent: *Jan. 30, 2024

(54) GROWING MEDIA EVALUATION SYSTEM AND METHOD

(71) Applicant: Predictive Nutrient Solutions, Inc., Walla Walla, WA (US)

(72) Inventors: Kristopher J. Borgman, Walla Walla, WA (US); Brennan A. Ingram, Battle Ground, WA (US)

(73) Assignee: Predictive Nutrient Solutions Inc., Walla Walla, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/079,793

(22) Filed: Dec. 12, 2022

(65) Prior Publication Data

US 2023/0114959 A1 Apr. 13, 2023

Related U.S. Application Data

(63) Continuation of application No. 17/665,983, filed on Feb. 7, 2022, now Pat. No. 11,525,821, which is a (Continued)

(51) Int. Cl.
*G01N 33/24* (2006.01)
*G01N 1/04* (2006.01)
(Continued)

(52) U.S. Cl.
CPC ........... *G01N 33/24* (2013.01); *A01C 21/007* (2013.01); *C09K 17/02* (2013.01); *G01N 1/04* (2013.01);
(Continued)

(58) Field of Classification Search
None
See application file for complete search history.

(56) References Cited

U.S. PATENT DOCUMENTS

2010/0121669 A1 5/2010 Madigan
2010/0143622 A1 6/2010 Schreuder
(Continued)

FOREIGN PATENT DOCUMENTS

CN 106779399 A 5/2017
EP 3327654 A1 5/2018

OTHER PUBLICATIONS

Ag PhD Soils Mobile Device App: Do-it-yourself soil sampling, https://agphdsoils.com/ [Date accessed: Oct. 15, 2019].
(Continued)

*Primary Examiner* — Daniel S Larkin
(74) *Attorney, Agent, or Firm* — Bold IP, PLLC (57) ABSTRACT

A system and method for evaluating soil characteristics. The system and method includes providing one or more soil test kits to a user. The soil tests kits may include ion-exchange resins and may instruct the user to collect a soil sample from his/her growing area, to combine the soil sample with the ion-exchange resins, and to provide the combination to the system for analysis. Other test kits may not include ion-exchange resins and may instruct the user to provide a soil sample from his/her growing area to the system for analysis. The system evaluates the ion-exchange resins and/or the soil samples to identify nutrient levels, pH levels, and other characteristics of the soil. Using the evaluation results, the system provides feedback, recommendations and/or products to the user to improve the soil conditions and to ensure a successful crop, yield, quality, and nutrient density. The system and method also may include providing a second soil test kit to the user at a predetermined time after the first, to evaluate a second soil sample, and to compare the second evaluation results with the first to assess the improvement of the soil conditions.

20 Claims, 8 Drawing Sheets

Related U.S. Application Data continuation of application No. 17/162,137, filed on Jan. 29, 2021, now Pat. No. 11,249,063.

(60) Provisional application No. 62/967,439, filed on Jan. 29, 2020.

(51) Int. Cl.
| | |
|---|---|
| *A01C 21/00* | (2006.01) |
| *G01N 33/2022* | (2019.01) |
| *C09K 17/02* | (2006.01) |
| *G06Q 50/02* | (2012.01) |
| *G06Q 30/0601* | (2023.01) |
| *G01N 33/2028* | (2019.01) |

(52) U.S. Cl.
CPC ..... *G01N 33/2022* (2019.01); *G01N 33/2028* (2019.01); *G06Q 30/0631* (2013.01); *G06Q 50/02* (2013.01); *G01N 2033/243* (2013.01); *G01N 2033/245* (2013.01)

(56) References Cited

U.S. PATENT DOCUMENTS

| | | |
|---|---|---|
| 2011/0240730 A1 | 10/2011 | Covely |
| 2014/0095074 A1 | 4/2014 | Covely |
| 2016/0270289 A1 | 9/2016 | Schildroth et al. |
| 2017/0045488 A1 | 2/2017 | Riess et al. |
| 2017/0108441 A1 | 4/2017 | Nault et al. |
| 2017/0178222 A1 | 6/2017 | High et al. |
| 2021/0048424 A1 | 2/2021 | Koshnick et al. |

OTHER PUBLICATIONS

Virginia Test Soil Testing Lab Website (soiltest vt.edu)—Oct. 21, 2017 (Wayback Machine/Intenet Archive), pp. 1-27 printed on Jun. 8-9, 2021.

Hue, N.V. et al., "Testing Your Soil: Why and How to Take a Soil-Test Sample", Soil and Crop Management, Cooperatve Extension Service, College of Tropical Agriculture and Human Resources, University of Hawai'i at manoa, Jul. 2004, pp. 1-4.

Clemson Regulatory Services Website (www.clemson.edu)—Dec. 2, 2017 (Wayback Machine/Internet Archive), pp. 1-3 printed on Jun. 10, 2021.

GROWING MEDIA EVALUATION SYSTEM AND METHOD

CROSS-REFERENCE TO RELATED APPLICATIONS

This application is a Continuation application of U.S. patent application Ser. No. 17/665,983 filed Feb. 7, 2022, now U.S. Pat. No. 11,525,821, which is a Continuation application of U.S. patent application Ser. No. 17/162,137 filed Jan. 29, 2021, now U.S. Pat. No. 11,249,063, the entire contents of all of which are hereby fully incorporated herein by reference for all purposes.

FIELD OF THE INVENTION

This invention relates to systems and methods for evaluating soil, including a soil test kit and automated soil sample evaluation and recommendation system.

BACKGROUND

Plants in natural soil environments absorb various nutrients through their roots from the surrounding soil in order to grow and thrive. If the soil surrounding a plant and its roots has been depleted of or otherwise does not provide sufficient vital nutrients, the plants may not survive, produce food, or provide their intended outcome(s). In addition, if the plants are being cultivated in non-soil growing media, the same requirements apply. Accordingly, when cultivating plants, assessing the nutrient content of the soil and/or other growing media is of the utmost importance to ensure a successful crop, yield, quality, and nutrient density.

However, many types of soil test systems currently available do not provide the accuracy necessary to achieve the best results. In addition, many of the available tests are difficult to understand and/or implement, and do not provide a start-to-finish solution for the hobbyist, amateur, and/or professional grower.

Accordingly, there is a need for an accurate soil testing system that is easy to understand and implement.

SUMMARY

According to one aspect, one or more embodiments are provided below for a system and method for evaluating growing media. The method of evaluation may include receiving from a third party at least one third party product list, providing a first growing media test kit to a user, the first growing media test kit including a growing media testing device, instructing the user to provide a first sample of growing media, evaluating the first sample of growing media to determine a first nutrient level of at least one nutrient and/or a first pH level, providing to the user results based at least in part on the evaluation, and providing to the user at least one product recommendation based at least in part on the evaluation, the at least one product recommendation chosen from the at least one third party product list.

In another embodiment, the providing to the user at least one product recommendation includes providing a link to at least one recommended product.

In another embodiment, the link includes an affiliate link to the at least one recommended product.

In another embodiment, the at least one recommended product includes a growing media amendment, a plant, a plant seed, a plant seedling, a plant pot, and soil.

In another embodiment, the growing media testing device includes at least one of an ion-exchange resin, an N-P-K test meter, a color metric strip, litmus paper, an LED color variation test device, a pH meter, a Mehlich-3 test device, a Bray test device, an Olsen test device, and saturated paste.

In another embodiment, instructing the user to provide a first sample of growing media further comprises providing guidance to the user regarding locating and/or collecting the sample of growing media.

In another embodiment, the guidance provided to the user includes guidance regarding at least one of: measuring a volume of a growing area, determining a quantity of growing media samples to collect given a volume of growing area, determining a depth at which a growing media sample is taken, and collecting growing media samples from a growing area.

In another embodiment, the providing the results in includes providing the results via a mobile application.

In another embodiment, the providing the at least one product recommendation includes providing the at least one product recommendation via a mobile application.

In another embodiment, the at least one nutrient includes at least one of nitrogen, phosphorus, potassium, sulfur, calcium, magnesium, sodium, iron, manganese, boron, copper, zinc, and aluminum.

According to another aspect, one or more embodiments are provided below for a system and method for evaluating growing media. The method of evaluation may include receiving from a third party at least one customization element selected from the group: a logo, contact information, and a color scheme, providing a first growing media test kit to a user, the first growing media test kit including a first growing media testing device, instructing the user to provide a first sample of growing media, evaluating the first sample of growing media to determine a first nutrient level of at least one nutrient and/or a first pH level, providing to the user results based at least in part on the evaluation, and providing to the user at least one product recommendation based at least in part on the evaluation, wherein the providing to the user results includes providing a report including the at least one customization element.

In another embodiment, the providing to the user at least one product recommendation includes providing a link to at least one recommended product.

In another embodiment, the link includes an affiliate link to the at least one recommended product.

In another embodiment, the at least one recommended product includes a growing media amendment, a plant, a plant seed, a plant seedling, a plant pot, and soil.

The presently disclosed system and method for evaluating growing media is more fully described in the detailed description below.

BRIEF DESCRIPTION OF THE DRAWINGS

Other objects, features, and characteristics of the present invention as well as the methods of operation and functions of the related elements of structure, and the combination of parts and economies of manufacture, will become more apparent upon consideration of the following description and the appended claims with reference to the accompanying drawings, all of which form a part of this specification. None of the drawings are to scale unless specifically stated otherwise.

DETAILED DESCRIPTION OF EXEMPLARY EMBODIMENTS

In general, and according to exemplary embodiments hereof, the system and method of the current invention provides a soil testing system 10. In some embodiments, the system 10 provides a growing media test kit (e.g., soil test kit, hydroponic solution test kit, etc.) to a user of the system 10. In other embodiments, the system 10 guides the user in the proper administration of the kit. In other embodiments, the system 10 analyzes the nutrient content and characteristics of the growing media samples collected by the kit and based on the results of the growing media analyses, provides results, feedback, and further guidance to the user.

In other embodiments, the system 10 may be used with growing media test kits provided to users by a different provider (e.g., a third party). In these embodiments, the system 10 may provide guidance to the user(s) for the proper administration of these third party kits, may analyze the nutrient content and characteristics of the media samples collected by the kits, and based on the results of the analyses, may provide results, feedback, and further guidance to the users of the third party kits. It is understood that the system 10 may be used in conjunction with any soil test kit, and that the scope of the system 10 is not limited in any way by the soil test kit that it may be used with.

In some embodiments, the soil test kits may include ion-exchange resins that the system 10 may use to measure relative amounts of plant-available nutrient ions in soil or hydroponic (solution and/or plant materials) samples and the rates at which the nutrients are released from soil, organic matter, solution, or other growing media. The resins may include ion-exchange resins (functionalized porous or gel polymers), zeolites, montmorillonite, clay, soil humus and/or other types of exchangers. The ion-exchangers may include negatively charged exchangers that capture negatively charged ions (anions), positively charged exchangers that capture positively charged ions (cations), and/or amphoteric exchangers that are able to exchange both cations and anions simultaneously. In other embodiments, the system 10 may be used with soil test kits that do not include resins.

In some embodiments, a user of the system 10 may add the ion-exchange resins provided by the soil test kit to samples of soil from his/her growing area and provide the combination to the system 10 for analysis. In other embodiments, a user may bury or place a sample of ion-exchange resins in his/her growing area and allow the resins to absorb nutrients from the soil or solution over a period of time as designed. In this case, because the resins may have absorbed an adequate amount of nutrients from the soil for testing, the user may provide the resins without the soil to the system 10 for analysis.

In other embodiments, a soil kit may not necessarily include ion-exchange resins, and the user may provide a sample of soil to the system 10 without resins. In this embodiment, the system 10 may add the resins to the sample of soil and perform the analysis. In other embodiments, the user may provide a sample of soil to a third party who may add the resins to the soil sample. In this embodiment, the third party may then provide the combination of soil and resins to the system 10 for analysis, may provide just the resins (after the resins have absorbed an adequate amount of nutrients from the soil sample for testing) to the system 10 for analysis, or any combination thereof. In other embodiments, the user may provide a sample of soil to the system 10 and the system 10 may test the nutrient level of the soil using methods that may not require ion-exchange resins as is known in the art and may choose not to add the ion-exchange resins to the soil sample prior to the analyses.

For the purposes of this specification however, details of the system 10 will be primarily described in relation to embodiments that include the user providing a soil sample combined with a sample of ion-exchange resins to the system 10 for analysis. However, it is understood that any combination of the methodologies describe herein also may be employed. It also is understood that the scope of the system 10 is not limited in any way regarding whether or not the ion-exchange resins are provided with the soil test kit, or not.

While it is understood that the system 10 may be utilized for evaluating soil and non-soil growing medias, for the purposes of this specification, the details of the system 10 will be described primarily in relation to soil medias. However, it is understood that the system 10 may be utilized to evaluate any type of growing media such as, without limitation, soil samples, hydroponic solutions, and other types of growing medias, as well as plant tissue, leaves, roots, shoots, and/or other plant material(s), and that the details described herein may pertain to any of these medias, items and/or elements. It also is understood that the scope of the system 10 is not limited in any way by the type of growing media and/or plant material(s) that it may be used to evaluate. It is also understood that the system 10 may be applied to any type of plant (e.g., edible and/or non-edible plants), and/or to any type of growing area (e.g., gardens, lawn/turf, conventional farming, urban farming, potted plants, and/or other types of growing areas), and that the scope of the system 10 is not limited in any way by the types of plants or the types of growing areas that it may be used with.

In some embodiments, the system 10 utilizes one or more testing facilities TFn to determine the levels of nitrogen (N), phosphorus (P), potassium (K), and other nutrients contained within soil sample(s) and/or ion-exchange resin samples provided by a user and depending on the type(s) of plant(s) being grown by the user, compares the measured levels to the ideal levels of each nutrient for each particular plant. In some embodiments, the system 10 determines the pH level of the soil sample and depending on the type(s) of plant(s) being grown, compares the measured pH level to the ideal pH level of the soil for each particular plant. The system 10 also may perform other tests to determine other characteristics of the soil, as necessary. The one or more test facilities TFn may be in-house, outsourced, or any combination thereof. In some embodiments, the test facilities TFn may provide onsite and/or real time analyses at the location of the growing area(s) (or otherwise "in the field") by utilizing on-location measurement and test equipment.

Once the soil sample tests have been performed, the system 10 may provide one or more reports (digitally, hardcopy, etc.) to the user showing the test results and providing recommendations to improve the quality of the soil or growing media. The system 10 also may provide additional guidance regarding the cultivation of the user's plants as well as visual aids and supporting information such as the different types of nutrients and the roles the nutrients play regarding plant health.

Figure 1:
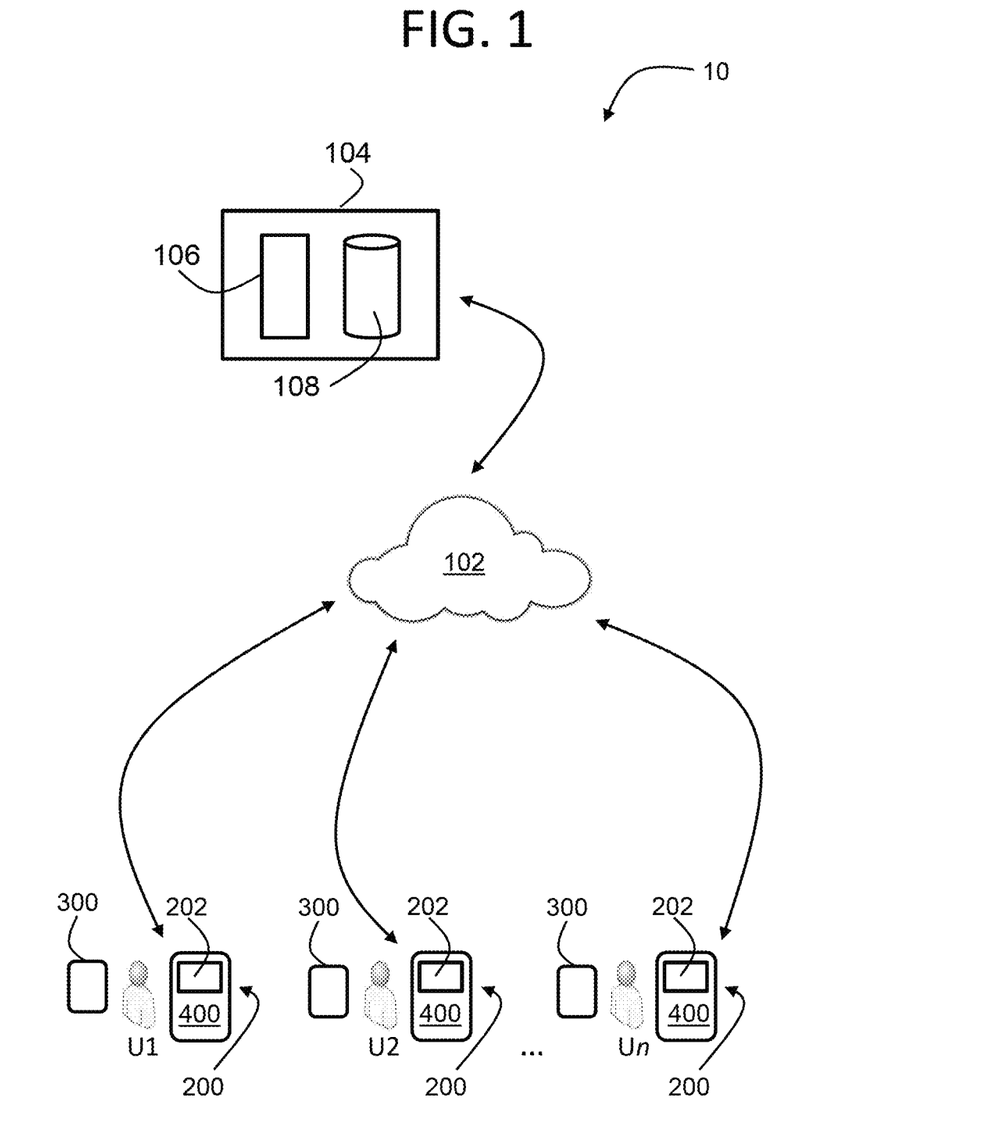
FIG. 1 shows an overview of a soil evaluation system in accordance with exemplary embodiments hereof.

In one exemplary embodiment hereof as shown in FIG. 1, the system 10 includes the following aspects (without limitation):

1. A backend infrastructure 100;
2. A frontend infrastructure 200;
3. A soil test kit 300; and
4. Other elements and/or components as required.

FIG. 1 shows an overview of an exemplary framework for a soil testing system 10 and method according to exemplary embodiments hereof. As shown, the system 10 includes a cloud platform 100 (also referred to as a backend) accessible through a network 102 such as the Internet, LAN, WAN, wireless communication systems, cellular communication systems, telephony, or other types of communication systems or protocols.

The cloud platform 100 may include one or more servers, one or more processors, memory, software, firmware, operating systems, a location determining mechanism (e.g., GPS), and other components and elements that may be necessary for the backend platform 100 to perform its functionalities as described herein.

The system 10 is accessed by multiple users U1, U2 . . . Un (e.g., via the network 102) using an application 202 (e.g., a mobile application or "app", a website browser or other types of applications, software program(s), widgets, scripts, etc.) running on one or more computing devices 400 (e.g., smart phones, tablet computers, laptops, desktop computers, mobile media players, etc.).

The cloud platform 100 may include one or more software systems 106 and one or more databases 108. The one or more software systems 106 may include operating systems, system software, web server software, social networking software, software applications, scripts, firmware, other types of software systems, and any combination thereof.

In general, and according to exemplary embodiments hereof, the backend 100 interfaces with the frontend 200 (e.g., with the mobile app 202) during the administration of the soil test kit 300, during the analysis of the soil sample(s) provided by the soil test kit 300, and during the reporting of the resulting data to the user Un.

It is understood that any element of the system 10 may be distributed across one or more platforms, backend systems 100, or frontend systems 200 and/or may be integrated into one or more platforms, backend systems 100, frontend systems 200 whether the systems 100, 200 are owned or otherwise controlled by the system 10, or not. For example, the system's backend 100 may be hosted on a third party's backend system, and/or the system's frontend system 200 (e.g., its mobile app 202) may be integrated into a third party's mobile application. Other elements of the system 10 may be integrated into third party websites, desktop applications, social widgets and/or any other type of third party system. When necessary, application programming interfaces (APIs) may be employed as is known in the art.

Figure 2:
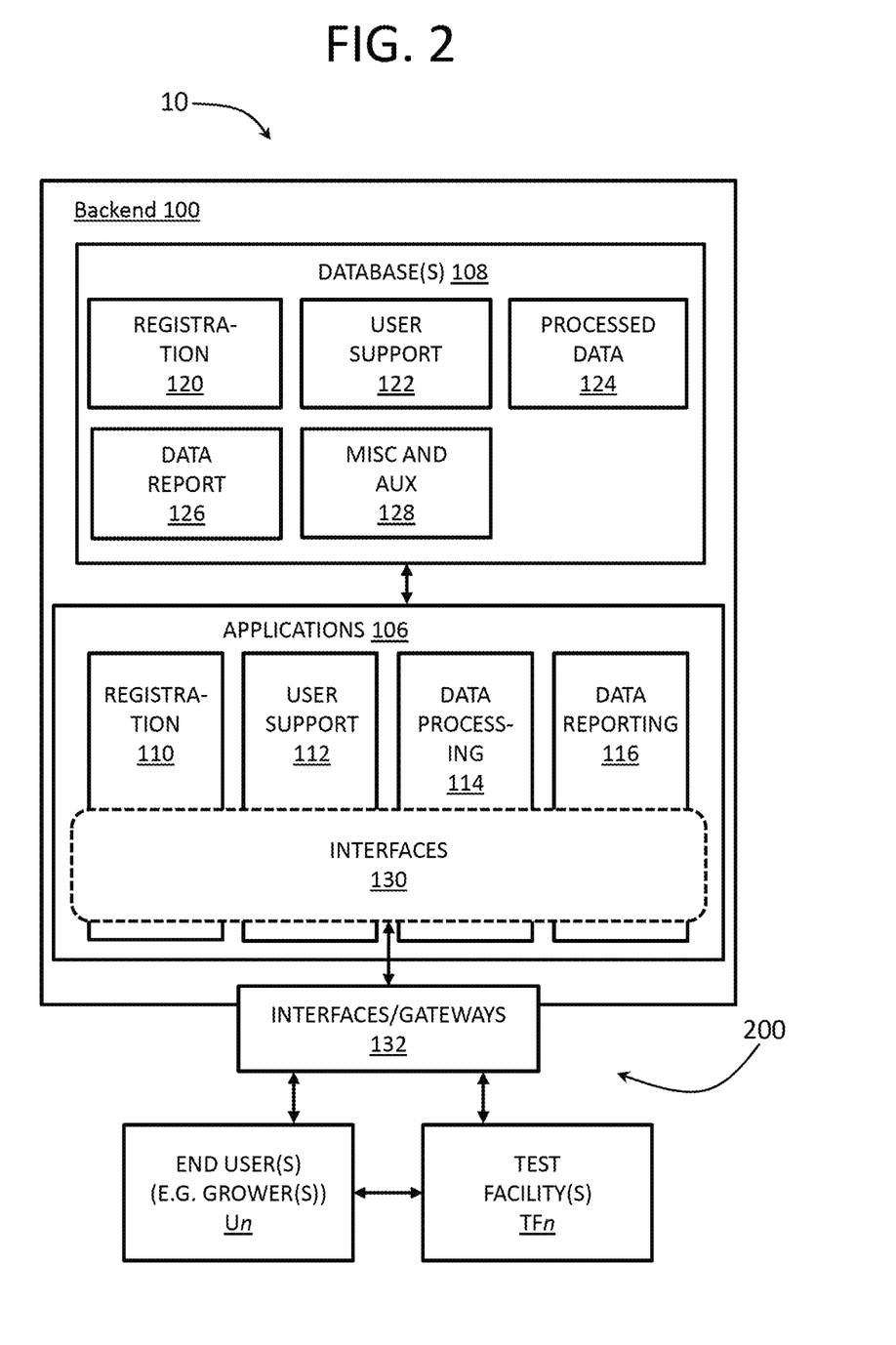
FIG. 2 shows aspects of a soil evaluation system in accordance with exemplary embodiments hereof.

FIG. 2 shows aspects of an exemplary soil testing system 10 of FIG. 1. As shown, the system 10 comprises various applications 106 and one or more databases 108, described in greater detail below. The applications 106 may generally interact with the one or more databases 108.

The database(s) 108 may be or comprise multiple separate or integrated databases, at least some of which may be distributed. The database(s) 108 may be implemented in any manner, and, when made up of more than one database, the various databases need not all be implemented in the same way. It should be appreciated that the system is not limited by the nature or location of database(s) 108 or by the manner in which they are implemented.

Each of the applications 106 may provide one or more services via an appropriate interface. Although shown as separate applications 106 for the sake of this description, it is appreciated that some or all of the various applications 106 may be combined. The various applications 106 may be implemented in any manner and need not all be implemented in the same way (e.g., using the same software languages, interfaces or protocols).

The applications 106 may include one or more of the following applications 106 (without limitation):

1. Soil test kit registration application(s) 110;
2. Soil test kit user support application(s) 112;
3. Data processing application(s) 114;
4. Data reporting application(s) 116; and
5. Other application(s) and/or auxiliary application(s).

Those of ordinary skill in the art will appreciate and understand, upon reading this description, that the above list of applications is meant for demonstration and that the system 10 may include other applications that may be necessary for the system 10 to generally perform its functionalities as described in this specification. For example, the system 10 may include a user registration application that collects the user's contact information during the creation of the user's account. In addition, as should be appreciated, embodiments or implementations of the system 10 need not include all of the applications listed, and that some or all of the applications may be optional. It is also understood that the scope of the system 10 is not limited in any way by the applications that it may include.

The database(s) 108 may include one or more of the following databases 108 (without limitation):

1. Registered soil test kit database(s) 120;
2. User support database(s) 122;
3. Processed data database(s) 124;
4. Data report database(s) 126; and
5. Miscellaneous and auxiliary database(s) 128.

It is understood that the above list of databases is meant for demonstration and that the system 10 may include some or all of the databases, and also may include additional databases as required. For example, the system 10 may include a users' account information database that stores each registered user's account information. It is also understood that the scope of the system 10 is not limited in any way by the databases that it may include.

Figure 3:
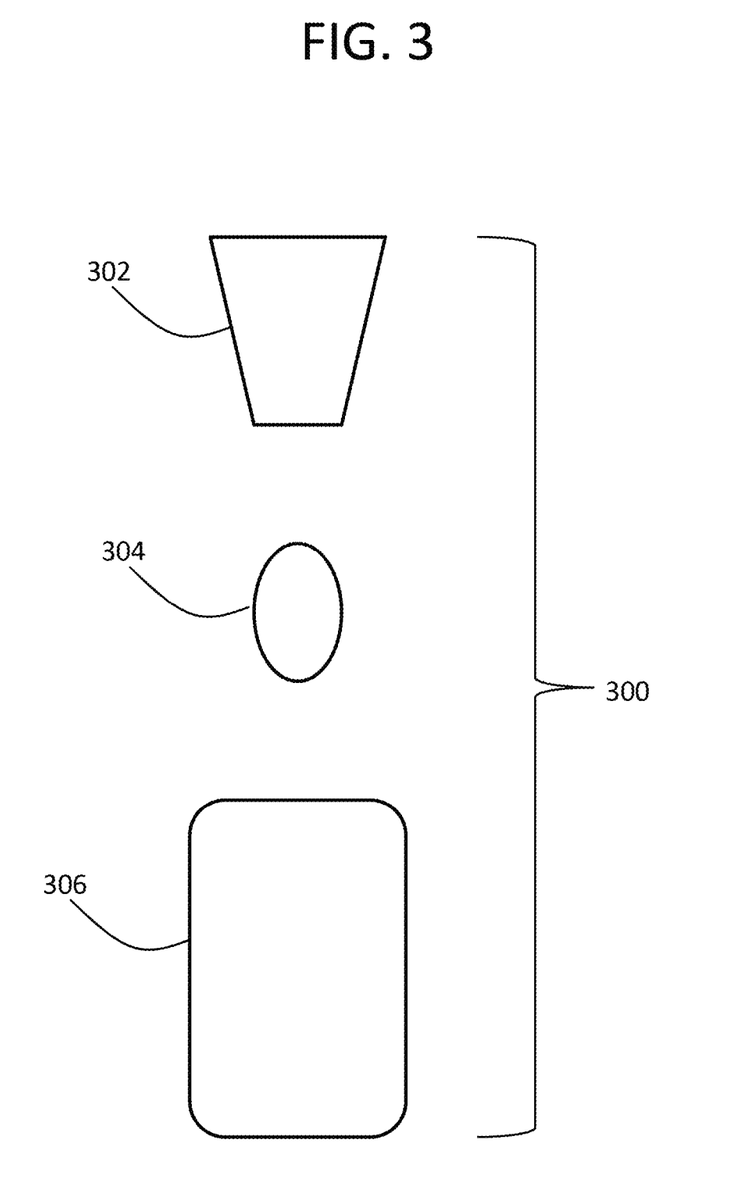
FIG. 3 shows aspects of a soil test kit in accordance with exemplary embodiments hereof.

Various applications 106 in the soil evaluation system 10 may be accessible via interface(s) 130. These interfaces 130 may be provided in the form of APIs or the like, made accessible to external users Un and/or test facilities TFn via one or more gateways and interfaces 132 (e.g., via a web-based application and/or an application (e.g., mobile app 202) running on a user's or test facility's device(s) 400). Access to the system 10 to third-party software and applications may also be provides through the use of APIs including XML-RPC, Modus, SOAP, JSON-RPC, REST, XLS and others Soil Test Kit In one exemplary embodiment hereof as shown in FIG. 3, the system 10 includes a soil test kit 300 that is provided to an end user Un to collect appropriate soil samples from the growing area of interest and to provide the samples to an appropriate test facility TFn for testing. The samples also may include other types of growing media such as samples of hydroponic nutrient solutions. The kit 300 may be provided through retail outlets, online ecommerce sites, associations, clubs, and/or through other channels.

In some embodiments, the soil test kit 300 may include the following elements (without limitation):

1. Soil collection container 302;
2. Ion-exchange resin(s) 304;
3. Shipping container 306;
4. Instructions and/or other documentation; and
5. Other components and/or elements, as necessary.

In some exemplary embodiments, the soil collection container 302 may comprise a jar, bottle, vial, box, bag, envelop, pouch, other type(s) of containers, and any combination thereof. The container 302 may comprise plastic, glass, metal, rubber, other materials, and any combination thereof. In general, the soil collection container 302 is of adequate size to contain an adequate sample size and to provide for the successful transport of the sample to an appropriate test facility TFn.

In some embodiments, the soil test kit 300 also may include an N-P-K meter/nutrient detection meter that provides a nutrient reading or pH reading, color metric strips, litmus paper, LED color variation testing, pH meter, solution-based "do-it-yourself" soil test kits, traditional nutrient soil extractions such as Mehlich-3, Bray, Olsen, Saturated Paste, and other elements.

In some exemplary embodiments, the ion-exchange resin(s) 304 include resins and/or polymers that provide a medium for ion exchange between the soil sample and the resin 304. As is known in the art, ion-exchange resins 304 may generally include an insoluble matrix (or support structure) normally in the form of small (0.25-0.5 mm radius) microbeads fabricated from organic polymer substrates. The beads are typically porous, providing a surface area for the trapping and releasing of ions (thus the term ion-exchange). The resins 304 may comprise crosslinked polystyrene sulfonate and or amine but other types of materials may also be used. It is understood that any type of adequate ion-exchange resins may be used and that the scope of the system 10 is not limited in any way by the type(s) of ion-exchange resins it may utilize. The resins also may be in the form of film, paper, strips and/or in other suitable forms.

As plants grow in natural soil environments, the plants' roots release hydrogen (H+) and hydroxide (OH—) ions in exchange for nutrients that may be available in the surrounding soil. The purpose of the ion-exchange resins 304 is to simulate this process by releasing the same types of ions (e.g., H+ and/or OH—) in exchange for the absorption of the available nutrients in the soil. In this way, the ion-exchange resins 304 may absorb a sample of nutrients from the soil or other growing media that may generally represent the same or similar levels of nutrients that the plants may absorb during daily nutrient acquisition in their natural growing environment.

In some embodiments, the system 10 may be utilized by a partnering user such as a third party brand, reseller, retailer or other type of vendor that may wish to sell or otherwise provide a soil test kit 300 or other services and/or elements of the system 10 to its customers. In this case, the system 10 may customize the soil test kits 300 to meet the users' needs. This may include branding the packaging, instructions, and/or other elements of the test kits 300 using the users' branding or other type(s) of identification. In these embodiments, the user may include an individual, a company, an association, an organization, and/or any other type of entity. For example, the system 10 may include a user's company logo on the packaging of the test kit 300, the user's contact information on the packing list as the provider of the kit 300, a particular color scheme that matches that of the user's brand, and/or other types of branding and/or customization elements in any area of the kits 300. In this way, at least a portion of the kits 300 (if not all) may be customized to appear as though they were created by the user's own brand. Other reasons and/or benefits of providing customized soil test kits 300 also may exist.

The System and Mobile Application—in Use

In some embodiments, it may be preferable that each user Un register with the system 10 to create a user account prior to utilizing the system 10. In this way, the system 10 may correlate the activity of each user Un with the associated user account. Registration and subsequent logins may occur through the mobile app 202, through associated websites, through third party applications or websites, via API transfers or by other suitable methods.

In one exemplary embodiment hereof, the system 10 and the mobile app 202 guide the user Un through the process of utilizing the system 10. In some embodiments, the mobile app 202 provides access to support materials (e.g., instructional videos, graphics, pictures, how-to instructions, FAQs, etc. stored within the user support database(s) 122) that may assist the user Un in collecting and preparing the soil sample(s). For example, the user support application(s) 112 may interface with the user support database(s) 122 to provide the instructional content to the user Un via the mobile app 202. For instance, the user support materials may instruct the user Un in the following ways (without limitation):

1. How to accurately measure the volume of the growing area;
2. Where to collect the soil samples within the growing area;
3. How many soil samples to collect given the size of the growing area;
4. The depth from which to retrieve the soil sample depending on the type(s) of plants being grown;
5. How to mix the soil sample with the ion-exchange resin 304;
6. How to prepare the shipping package 306 for shipping the sample;
7. How to register the soil sample with the system 10; and
8. Other support subjects, as necessary.

In addition, the user support application 112 may provide live chat, messaging, video conferencing, phone calls and/or other types of interactive applications via the frontend infrastructure 200 (e.g., the mobile app 202) that facilitate interaction between the users Un and the system 10. In some cases, this may involve interfacing with a live human expert that may provide guidance directly to the users Un regarding use of the system 10 and answers to questions regarding agronomy and other related topics. In other cases, this may involve artificial intelligence systems that may provide the information to the users Un.

In one step, the kit 300 may provide the user Un a QR code, a barcode, or other types of identifying elements that the user Un may scan using the mobile app 202 to register his/her specific kit 300 with the system 10. For example, the kit 202 may include a distinct code (barcode, QR code, etc.)

that when scanned uniquely identifies the distinct kit 300 and the associated soil sample with the system 10 and the associated user Un. The user Un also may provide other information to the system 10 during registration using the app 202 such as contact information, soil sample identification information, type of crop and/or plants being grown, sample date, and other types of information. The system 10 may utilize the soil test kit registration application 110 and store the registration information into the registered soil test kit database 120. In this way, the unique kit 300 and associated soil samples obtained from a particular user Un may be tied directly to the corresponding test results, test reports, recommendations, suggested products, customized products, guidance, etc.

In a second step, the mobile app 202 may guide the user Un through the process of characterizing the growing area and collecting an appropriate soil sample. This may include determining the dimensions of the growing area. In some embodiments, the app 202 utilizes a camera associated with the mobile device 400 and determines the dimensions of the growing area by applying measurement algorithms to images (e.g., photographs, video, etc.) of the growing area captured by the camera.

In some embodiments, the system 10 may calculate geospatial information of the growing area (e.g., using GPS) and utilize maps (e.g., open sourced, purchased, etc.) to help determine the proper area(s) to collect the samples. For applications where the growing area is large (e.g., more than one-eighth acre), the system 10 may recommend taking a plurality of samples at different locations across the area to form a composite sample set. The system 10 may also underlay soil maps (e.g., open source, purchased, etc.) to better determine the depth at which to collect the samples.

In some embodiments, the system 10 may recommend specialized soil collection tools as needed for specific types of growing areas and conditions.

In some embodiments, the app 202 includes augmented reality application(s) and places computer-generated perceptual information such as images, videos, graphics, etc. onto the image(s) and/or video(s) of the growing area captured by the device's camera. These augmented images may include graphical targets showing the user Un where to collect the soil samples, the depth to dig, and other types of guidance.

Once the soil samples are collected, the app 202 may guide the user Un through the process of mixing the soil samples with the ion-exchanging resins 304 to create a saturated paste or slurry. In some embodiments the soil samples may be field-moist and may be subsequently saturated with water and/or deionized water. However, this may not be required.

As described above, in some embodiments, the ion-exchange resins 304 may be buried within user's growing area for a sufficient amount of time as designed and may be provided to the system 10 without the accompanying soil samples.

Once the samples have been collected and combined with the ion-exchanging resin 304, the collection container 302 may be sealed and placed into the shipping container 306 and transported to the testing facility TFn. In some embodiments, the app 202 may provide tracking information with daily updates regarding the shipping process. The app 202 may also notify the user Un when his/her shipment has arrived and received by the testing facility TFn (e.g., scanned/accepted).

Upon receipt of the soil samples and/or associated resins 304, the system 10 may conduct a wide variety of tests on the soil samples and/or associated ion-exchanging resins 304 to determine the nutrient content, pH levels, and other characteristics of the samples. It is understood that in some embodiments the system 10 may test the soil sample(s) directly using conventional methods, while in other embodiments the system 10 may test samples of ion-exchanging resins 304 that may be associated with one or more samples of soil. In some embodiments, the system 10 tests the samples for levels of nitrogen (N) (for both the nitrate and ammonium forms), phosphorus (P), potassium (K), sulfur (S), calcium (Ca), magnesium (Mg), sodium (Na), iron (Fe), manganese (Mn), boron (B), copper (Cu), zinc (Zn), aluminum (Al), and other nutrients. The system 10 also may test the soil biology bacteria—Active (AB) and Total (TB), Fungi—Active (AF) and Total (TF), Protozoa (PROTS)—*Flagellates* (F), Amoebae (A), Ciliates (C), Nematodes (NEM), Nitrogen Cycling Potential (lbs./ac), Mycorrhizal Colonization (MC), ENDO, ECTO and ERICOID, *Verticillium, Pythium-Phytophthora-Fusarium*, and others.

In some embodiments, the system 10 also may perform other types of chemical and physical soil analysis including percentage sand silt clay, percentage CEC, percentage organic matter, pH, water infiltration, compaction, respiration, $CO_2$ release, and others.

The system 10 may utilize the data processing application 114 to process the data and store it to the processed data database 124. In this way, the influence of soil pH, biology, and mineralogy on nutrient availability may be assessed by measuring the quantity of specific nutrients and/or pH levels in each resin sample, in each sample of growing media (e.g., soil samples, hydroponic solution samples) or other types of test media. As this process is performed, the system 10 may provide alerts, status updates and/or other types of correspondence to the corresponding user Un to keep the user Un informed on one or more portions of the sample and testing progress.

Next, the system 10 may collect the appropriate processed data and generate one or more data reports using the data reporting application 116. The data reports may be provided to the users Un via the mobile app 202, in digital form through email, as hardcopy (e.g., through the mail), or by other means, and stored in the data report database 126 to be retrieved at any time.

In some embodiments, the reports depict the measured levels of each nutrient in the soil sample, the ideal levels of each nutrient given the types of plants or crops that the user Un is growing, and other relevant information. In general, each nutrient level in each soil sample may be shown as too high, too low, or generally adequate for ideal plant growth. This information may improve plant health and quality while increasing sustainability and reducing environmental impacts. Stewardship reports may also be provided.

In some embodiments, the system 10 may be utilized by a partnering user such as a third party brand, reseller, retailer or other type of vendor that may wish to sell or otherwise provide a soil test kit 300 or other services and/or elements of the system 10 to its customers. In these embodiments, the system 10 customizes the reports to meet the users' needs. This may include branding the reports using the users' branding or other type(s) of identification. In these embodiments, the user Un may include an individual, a company, an association, an organization, and/or any other type of entity. For example, the system 10 may include a user's company logo in the header of the report(s), the user's contact information as the provider of the report, a particular color scheme that matches that of the user's brand, references to specific product lines (e.g., to a specific brand of soil amendment products) or lists, and/or other types of branding and/or customization elements in any area of the reports. In this way, at least a portion of the report (if not all) may be customized to appear as though it were created by the user's own brand. Other reasons and/or benefits of providing customized reports also may exist. The customized reports may include digital reports, hardcopy reports, other types of reports, any type(s) of feedback or communications, and any combinations thereof.

In some embodiments, the system 10 provides recommendations to the user Un that may be used to improve the quality of the soil within the growing area based on the results of the testing. For example, the system 10 may recommend using a specific type and amount of fertilizer and/or new soil to increase the levels of one or more deficient nutrients in the growing area. In this example, the fertilizer-soil amendment may be organic, synthetic, liquid, granular or a blend of any combination thereof.

In another example, the system 10 may recommend adjusting the pH level of the growing area soil by adding a specific amount of one more specific pH level modifiers. In another example, the system 10 may provide additional soil amendment guidance such as the inclusion of wetting agents based on the nutrient location depth detected by the soil sample tests. In another example, the system 10 may recommend additional chemical, herbicide, fungicide, and/or other types of applications including ROUNDUP® type products based on the soil sample test results or user provided information such as grass/weed type.

Knowing the characteristics of the growing area including its size, location, the depths at which the samples were taken and the results of the soil sample tests, the system 10 may provide the recommended levels and rates at which to add the fertilizers and/or soil amendments (based on product size, density, weight, distribution, coverage, etc.), the process(es) used to apply the products (e.g., the sprayer/spreader, fertigation, nozzle size and its associated settings), the depth at which to apply the products, and other pertinent information. This may include daily, weekly, monthly, yearly and/or other frequency plans based on the specific test results of each soil sample or a comparison of multiple samples over time.

The system 10 may make other types of recommendations for other types of amendments and it is understood that the scope of the system 10 is not limited in any way by the types of tests the system 10 performs and/or the types of recommendations that the system 10 provides.

In some embodiments, the system 10 may provide for the purchase or acquisition of the recommended products (e.g., fertilizers or other soil amendments) by offering the products for sale through the mobile app 202 or via API transfer from lab platform LIMS to $3^{rd}$ party mobile apps, on associated ecommerce websites, directly from the supplier and/or affiliates, affiliate purchase links, or through other channels. In other embodiments, the system 10 may guide the users Un to the proper retail outlet to purchase the products while providing product availability based on store location and local inventory levels and the ability to purchase based on pricing options for similar products. In some embodiments, the system 10 may make available for purchase or acquisition other types of products, such as, without limitation, plant seeds, plant starts, trees, pots, soil, other types of products, and/or any combinations thereof.

In some embodiments, the system 10 may provide notifications and/or alerts for continued maintenance and/or testing practices on a daily, weekly, monthly, quarterly, yearly, or other frequency basis. In some instances, the system 10 may recommend the retesting of the growing area soil at one or more locations and/or depths using a new soil testing kit 300, after which, the new results may be compared to the prior results so that any additional modifications to the soil treatment plan may be made based on the new test and comparison data. Because the system 10 stores all test results in perpetuity (or for at least the term of each respective user's subscription) in the processed data database 124 and/or the data report database 126, comparisons may be made at any frequency such as year-to-year, sample-to-sample, nutrient-to-nutrient and at each location, for each crop, etc. Modifications to the soil treatment plans may be made on a case-by-case basis and may pertain directly to the location(s) and depths of the soil sample sites and/or the types of plants/crops being cultivated. These alerts and updates also may be provided to support each user's goals for the associated time periods.

Note also that the system 10 may be used to test a soil sample collected from a first location (e.g., a front yard) and a soil sample collected from a second location (e.g., a backyard) and to compare the test results between the soils of the first and second locations. In this way, the system 10 may provide the comparison results to the user with recommendations for one or both of the growing locations. This also may be performed over various time intervals as discussed above. In addition, the system 10 may be used to test a soil sample collected from a growing area of a first crop type and a soil sample collected from a growing area of a second crop type, and to compare the test results between the crop types. Other types of comparisons also may be performed in any combination.

In some embodiments, the system 10 provides the mechanisms (e.g., through the app 202) for each user Un to upload images, photographs, videos and/or other types of media to the appropriate database(s) 108 to document his/her cultivation of plants, to track his/her progress, to share his/her progress with other growers and/or for other purposes.

In some embodiments, the system 10 may provide other types of guidance such as tillage and cultivation practices based on nutrient location depth(s) evaluated by each soil test kit data. The system 10 also may help minimize the volatilization, leaching, eutrophication, and/or run-off of recommended nutrients and amendments by analyzing soil data associated with infiltration rates, percolation rates, and soil type (e.g., percent sand, silt, clay and/or organic matter), and by providing recommendations for appropriate irrigation practices. For example, the system 10 may provide guidance and information (e.g., specifications, usage data, APIs, etc.) pertaining to irrigation sensors/systems, soil moisture sensors/probes, and other types of systems in combination with other types of guidance as described in other sections.

In some embodiments, the system 10 may provide and/or recommend soil amendments, fertilizer(s), or other elements preformulated for particular applications for particular users. For example, the system 10 may provide and/or recommend a particular fertilizer preformulated to match the needs of the user Un accompanied by data pertaining to the fertilizer and/or the predicted soil outcomes that a user Un may expect when using the fertilizer. Data may be attained through artificial intelligence (AI) and/or by pre-testing fertilizer and soil amendment products in different soil types to build a database of data or a "center of excellence". For instance, the system 10 may provide data associated with a specific fertilizer's release characteristics (e.g., data curves representing product release at 2 weeks, 4 weeks, 8 weeks, etc.) over a known period of time. In another example, the provided information may include predicted pH level changes that a user Un may expect when using a particular preformulated pH level modifier. It is understood that other types of data may also be provided.

In some embodiments, the system 10 uses the results of an analysis for a particular user Un to produce, manufacture, blend, package, acquire, or otherwise provide to the particular user Un the soil amendments, fertilizers, and/or other products that may assist the user Un in implementing the suggestions and recommendations provided to the user Un by the system 10. This may include creating one or more customized products (e.g., custom blends of amendments, soils, fertilizers, etc.) for a particular user Un to meet that user's needs, acquiring such products from other sources and providing them to the user Un, and any combinations thereof. This may include the products themselves, as well as the packaging, bags, boxes, jugs, containers, tools, and/or other relevant elements that may accompany the products. The products may be liquid, solid, gaseous, granular, synthetic, organic, soluble, and/or in other forms. The products may be made available to the user Un for sale through the mobile application 202, through ecommerce websites, through wholesale outlets, through retail outlets, through other channels, and any combinations thereof.

It is understood that any of the details described herein pertaining to the system 10 providing recommendations and/or products to a user based at least in part on analyses of test data may apply to instances wherein (i) the system 10 provides the soil test kits 300 and performs the subsequent tests and analyses, (ii) the system 10 provides the soil test kits 300, a third party performs the subsequent tests, provides the test results to the system 10, and the system 10 performs the subsequent analyses, (iii) a third party provides the soil test kits 300, performs the tests and provides the test results to the system 10 which performs the analyses, (iv) a third party provides the soil test kits and the system 10 performs the tests and the analyses, and/or (v) any combination thereof.

In some embodiments, the system 10 may interface with outside systems (e.g., manufacturers of the products) to obtain the data provided to the users Un, or the system 10 may perform tests on the products to determine the data in-house.

In some embodiments, the system 10 may utilize climate modeling techniques (open source, paid, etc.) to consider weather conditions such as rain/irrigation, wind, temperature, humidity, and other conditions to provide effective and sustainable application guidance to each individual user Un.

In some embodiments, the system 10 provides guidance on the types of seeds, varieties, rates, depths, densities, populations, and other aspects based on the results of the soil tests analyses.

In some embodiments, the system 10 is synched with product providers that may provide information on various products that the system 10 may recommend to its users Un. This may include information on new product releases, new data sheets for new products, and/or other information.

In some embodiments, the system 10 may combine the processed data from the soil test kits 300 with conventional soil test data from conventional soil test systems (e.g., that include methods of drying and/or grinding soil or suction of saturated soil solutions) to further increase the comprehensiveness of the guidance it may provide to its users Un.

In some embodiments, the system 10 may interface with other systems (e.g., other soil testing facilities) to share data that may be applicable and/or relevant to the system's users Un (e.g., other soil test data that a user Un may have acquired through other programs). In addition, data from other sources (or from the users themselves) may be manually entered into the system 10 as required.

In some embodiments, the system 10 may be used to test and provide guidance for controlled environment agriculture, including the temperature of the facility, leaf temperature, airflow, humidity, soil temperature, soil moisture, fertigation/irrigation, CEC, organic matter, hydroponic solution content, temperature and flow, and other pertinent aspects.

Figure 4:
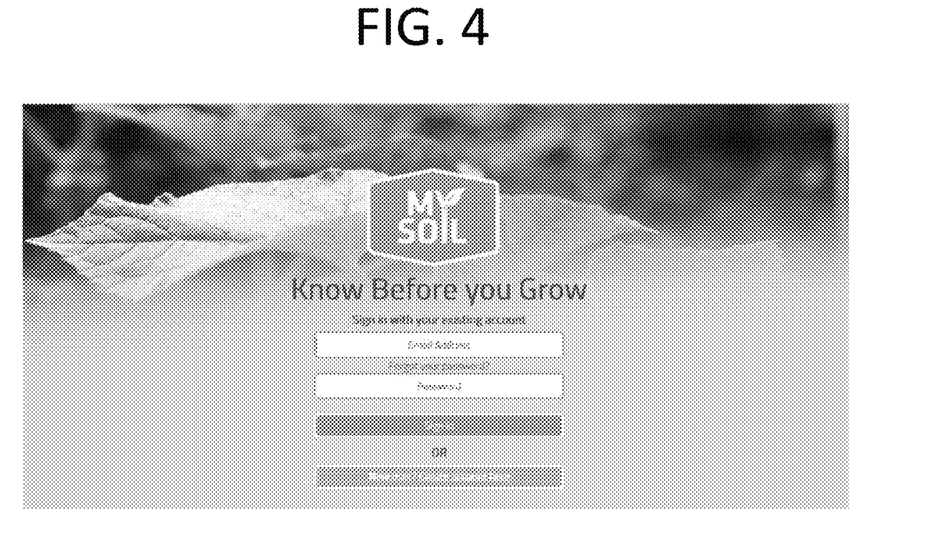
FIG. 4 shows an example user system log-in dialog in accordance with exemplary embodiments hereof.
Figure 5:
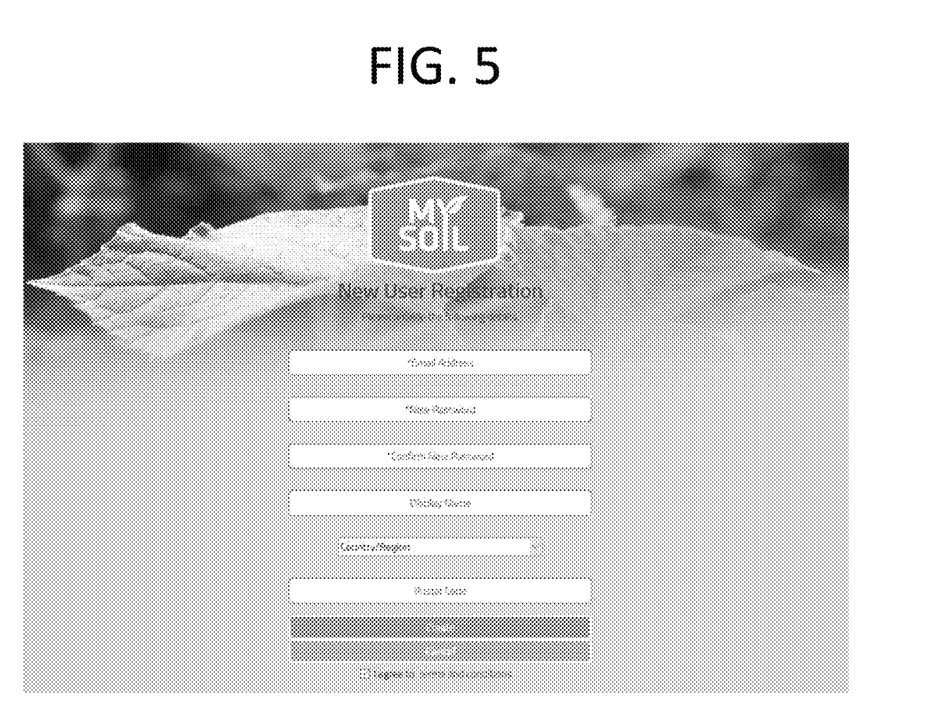
FIG. 5 shows an example user system registration dialog in accordance with exemplary embodiments hereof.
Figure 6:
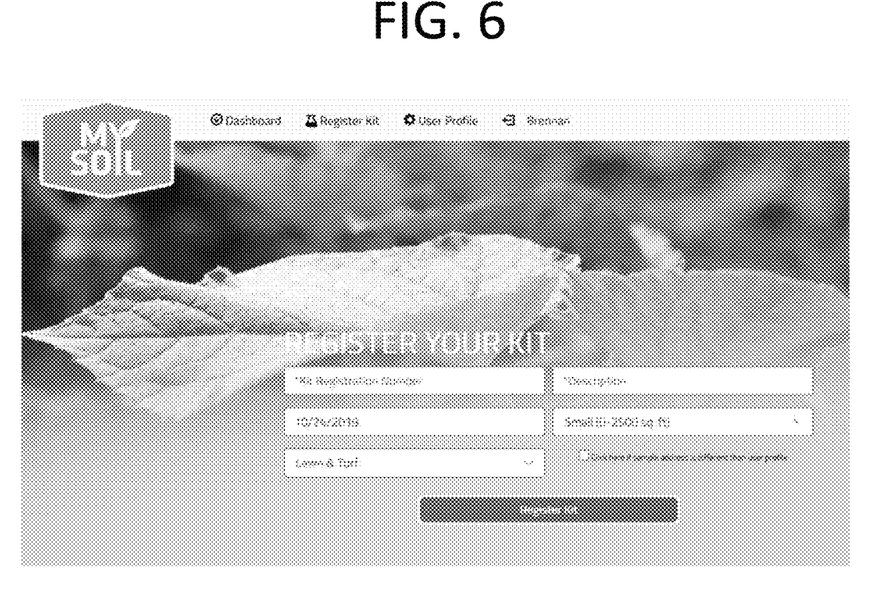
FIG. 6 shows an example soil kit sample kit registration dialog in accordance with exemplary embodiments hereof.
Figure 7:
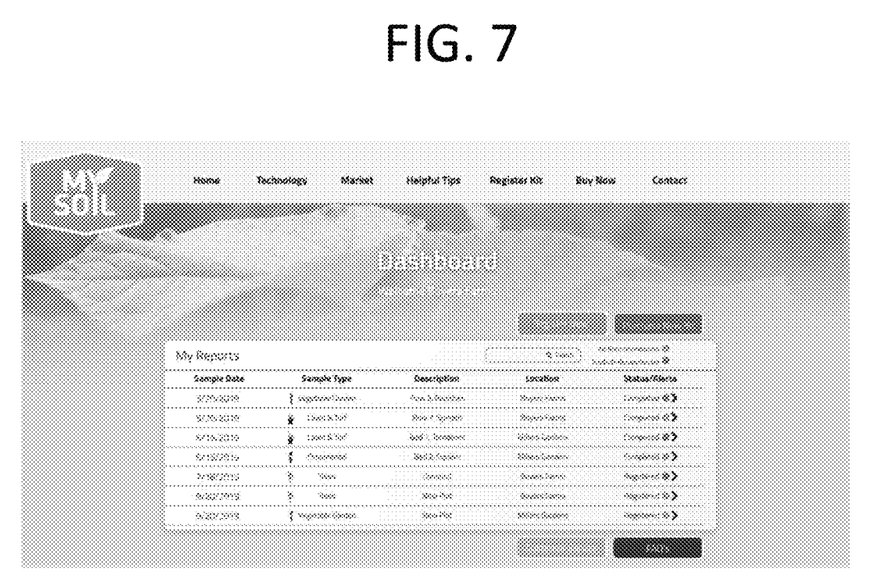
FIG. 7 shows an example desktop user dashboard in accordance with exemplary embodiments hereof.
Figure 8:
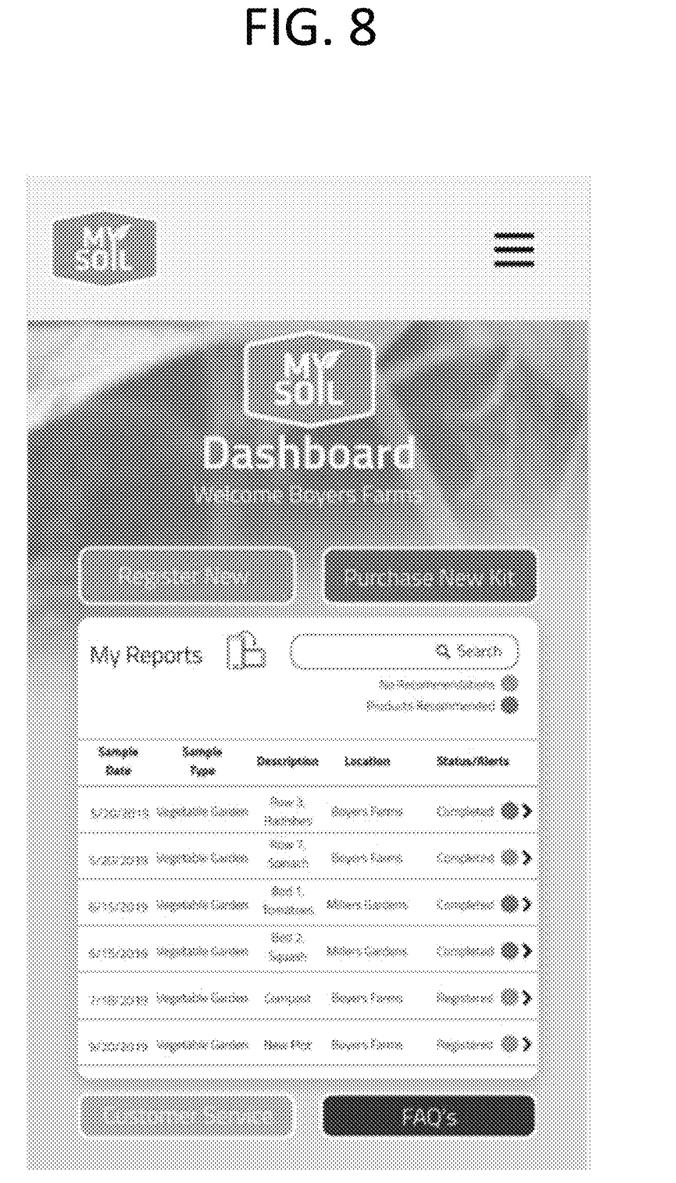
FIG. 8 shows an example mobile user dashboard in accordance with exemplary embodiments hereof.
Figure 9:
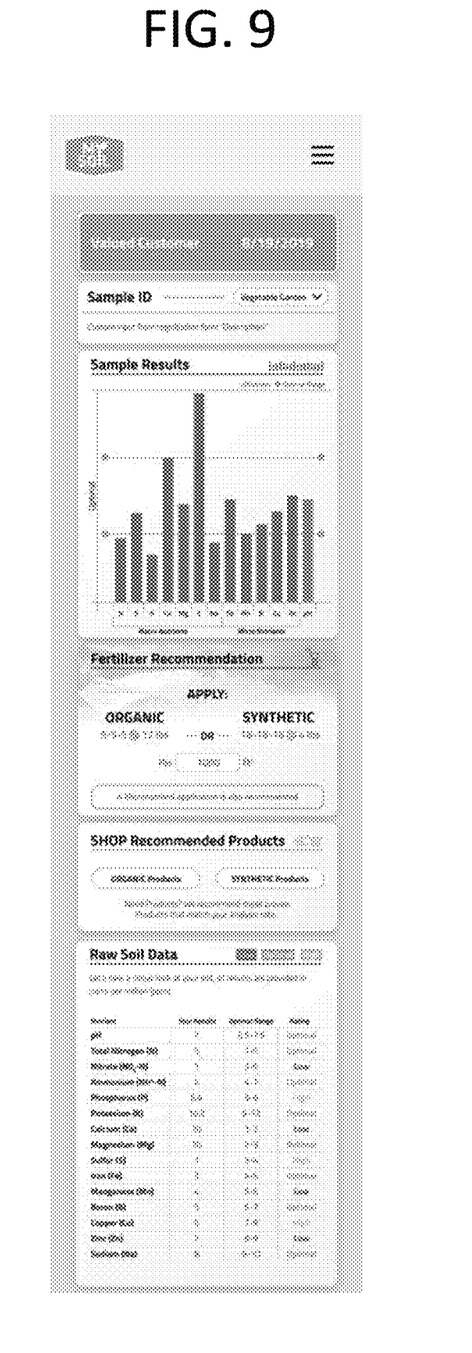
FIG. 9 shows aspects of a soil evaluation in accordance with exemplary embodiments hereof.

In some embodiments, the frontend 200 (e.g., the mobile app 202) includes a variety of graphical user interfaces (GUIs), dialogues, interfaces, and other elements that the user Un may interact with while using the system 10. For example, FIG. 4 depicts an example user Un log-in page, FIG. 5 depicts an example user Un registration page, FIG. 6 depicts an example soil sample kit registration page, FIG. 7 depicts an example desktop user Un dashboard, FIG. 8 depicts an example mobile user Un dashboard, and FIG. 9 depicts example soil sample test reports (e.g., mobile app 202 versions). It is understood that these example user dialogs are for demonstration purposes and that the system 10 may include any type(s) of user dialogs and that the scope of the system 10 is not limited in any way by the user dialogs that it may provide.

It is understood that any aspect, element, or component of any embodiment of the system 10 described herein may be combined with any other aspect, element, or component of any other embodiment of the system 10 to form additional embodiments of the system 10 all of which are within the scope of the system 10.

Computing

The services, mechanisms, operations, and acts shown and described above are implemented, at least in part, by software running on one or more computers or computer systems or devices. It should be appreciated that each user device is, or comprises, a computer system.

Programs that implement such methods (as well as other types of data) may be stored and transmitted using a variety of media (e.g., computer readable media) in a number of manners. Hard-wired circuitry or custom hardware may be used in place of, or in combination with, some or all of the software instructions that can implement the processes of various embodiments. Thus, various combinations of hardware and software may be used instead of software only.

One of ordinary skill in the art will readily appreciate and understand, upon reading this description, that the various processes described herein may be implemented by, e.g., appropriately programmed general purpose computers, special purpose computers and computing devices. One or more such computers or computing devices may be referred to as a computer system.

Figure 10:
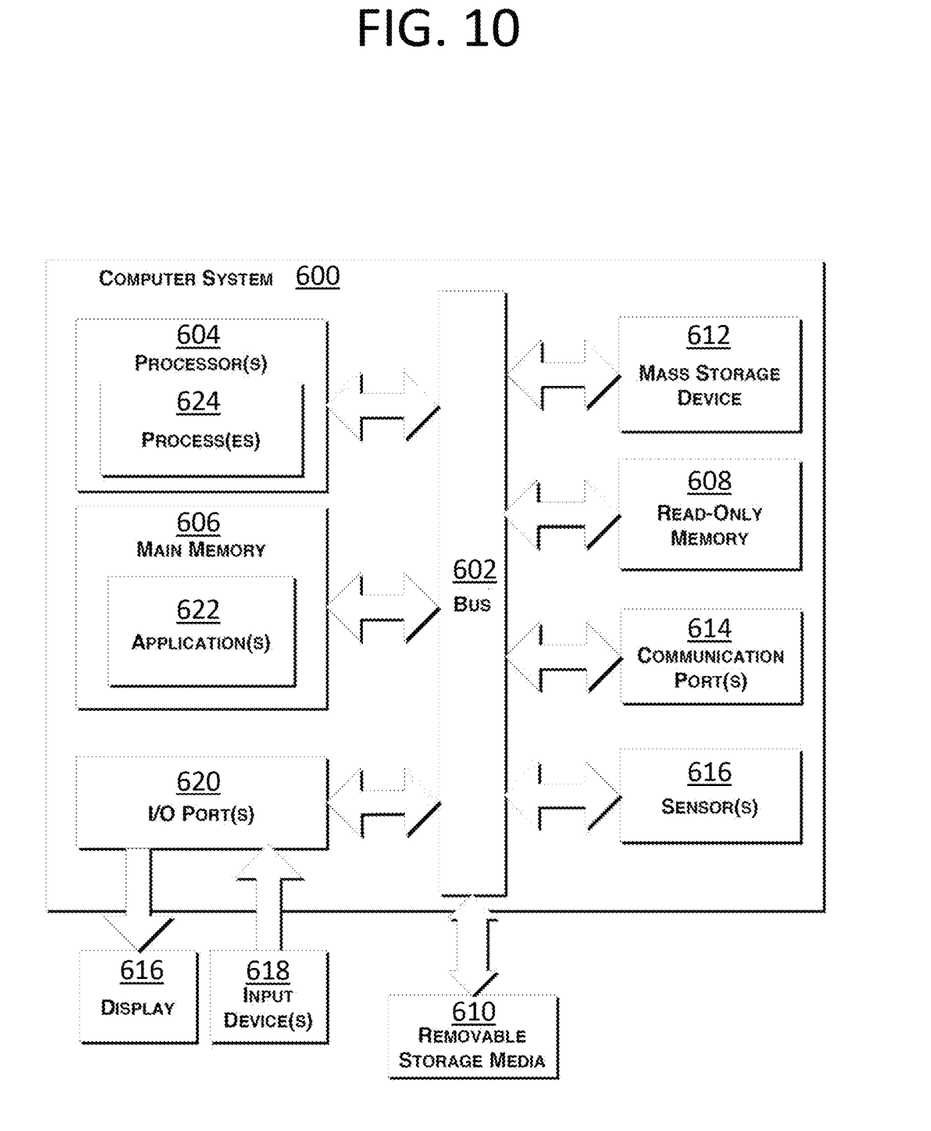
FIG. 10 depicts aspects of computing and computer devices in accordance with exemplary embodiments hereof.

FIG. 10 is a schematic diagram of a computer system 600 upon which embodiments of the present disclosure may be implemented and carried out.

According to the present example, the computer system 600 includes a bus 602 (i.e., interconnect), one or more processors 604, one or more communications ports 614, a main memory 606, removable storage media 610, read-only memory 608, and a mass storage 612. Communication port(s) 614 may be connected to one or more networks by way of which the computer system 600 may receive and/or transmit data.

As used herein, a "processor" means one or more microprocessors, central processing units (CPUs), computing devices, microcontrollers, digital signal processors, or like devices, or any combination thereof, regardless of their architecture. An apparatus that performs a process can include, e.g., a processor and those devices such as input devices and output devices that are appropriate to perform the process.

Processor(s) 604 can be (or include) any known processor, such as, but not limited to, an Intel® Itanium® or Itanium 2® processor(s), AMD® Opteron® or Athlon MP® processor(s), or Motorola® lines of processors, and the like. Communications port(s) 614 can be any of an RS-232 port for use with a modem-based dial-up connection, a 10/100 Ethernet port, a Gigabit port using copper or fiber, or a USB port, and the like. Communications port(s) 614 may be chosen depending on a network such as a Local Area Network (LAN), a Wide Area Network (WAN), a CDN, or any network to which the computer system 600 connects. The computer system 600 may be in communication with peripheral devices (e.g., display screen 616, input device(s) 618) via Input/Output (I/O) port 620. Some or all of the peripheral devices may be integrated into the computer system 600, and the input device(s) 618 may be integrated into the display screen 616 (e.g., in the case of a touch screen).

Main memory 606 can be Random Access Memory (RAM), or any other dynamic storage device(s) commonly known in the art. Read-only memory 608 can be any static storage device(s) such as Programmable Read-Only Memory (PROM) chips for storing static information, such as instructions for processor(s) 604. Mass storage 612 can be used to store information and instructions. For example, hard disks such as the Adaptec® family of Small Computer Serial Interface (SCSI) drives, an optical disc, an array of disks such as Redundant Array of Independent Disks (RAID), such as the Adaptec® family of RAID drives, or any other mass storage devices may be used.

Bus 602 communicatively couples processor(s) 604 with the other memory, storage, and communications blocks. Bus 602 can be a PCI/PCI-X, SCSI, a Universal Serial Bus (USB) based system bus (or other) depending on the storage devices used, and the like. Removable storage media 610 can be any kind of external hard-drives, floppy drives, IOMEGA® Zip Drives, Compact Disc-Read Only Memory (CD-ROM), Compact Disc-Re-Writable (CD-RW), Digital Versatile Disk-Read Only Memory (DVD-ROM), etc.

Embodiments herein may be provided as one or more computer program products, which may include a machine-readable medium having stored thereon instructions, which may be used to program a computer (or other electronic devices) to perform a process. As used herein, the term "machine-readable medium" refers to any medium, a plurality of the same, or a combination of different media, which participate in providing data (e.g., instructions, data structures) which may be read by a computer, a processor, or a like device. Such a medium may take many forms, including but not limited to, non-volatile media, volatile media, and transmission media. Non-volatile media include, for example, optical or magnetic disks and other persistent memory. Volatile media include dynamic random-access memory, which typically constitutes the main memory of the computer. Transmission media include coaxial cables, copper wire and fiber optics, including the wires that comprise a system bus coupled to the processor. Transmission media may include or convey acoustic waves, light waves, and electromagnetic emissions, such as those generated during radio frequency (RF) and infrared (IR) data communications.

The machine-readable medium may include, but is not limited to, floppy diskettes, optical discs, CD-ROMs, magneto-optical disks, ROMs, RAMs, erasable programmable read-only memories (EPROMs), electrically erasable programmable read-only memories (EEPROMs), magnetic or optical cards, flash memory, or other type of media/machine-readable medium suitable for storing electronic instructions. Moreover, embodiments herein may also be downloaded as a computer program product, wherein the program may be transferred from a remote computer to a requesting computer by way of data signals embodied in a carrier wave or other propagation medium via a communication link (e.g., modem or network connection).

Various forms of computer readable media may be involved in carrying data (e.g. sequences of instructions) to a processor. For example, data may be (i) delivered from RAM to a processor; (ii) carried over a wireless transmission medium; (iii) formatted and/or transmitted according to numerous formats, standards or protocols; and/or (iv) encrypted in any of a variety of ways well known in the art.

A computer-readable medium can store (in any appropriate format) those program elements that are appropriate to perform the methods.

As shown, main memory 606 is encoded with application(s) 622 that support(s) the functionality as discussed herein (an application 622 may be an application that provides some or all of the functionality of one or more of the mechanisms described herein). Application(s) 622 (and/or other resources as described herein) can be embodied as software code such as data and/or logic instructions (e.g., code stored in the memory or on another computer readable medium such as a disk) that supports processing functionality according to different embodiments described herein.

During operation of some embodiments, processor(s) 604 accesses main memory 606 via the use of bus 602 in order to launch, run, execute, interpret or otherwise perform the logic instructions of the application(s) 622. Execution of application(s) 622 produces processing functionality of the service(s) or mechanism(s) related to the application(s). In other words, the process(es) 624 represents one or more portions of the application(s) 622 performing within or upon the processor(s) 604 in the computer system 600.

It should be noted that, in addition to the process(es) 624 that carries(carry) out operations as discussed herein, other embodiments herein include the application 622 itself (i.e., the Un-executed or non-performing logic instructions and/or data). The application 622 may be stored on a computer readable medium (e.g., a repository) such as a disk or in an optical medium. According to other embodiments, the application 622 can also be stored in a memory type system such as in firmware, read only memory (ROM), or, as in this example, as executable code within the main memory 606 (e.g., within Random Access Memory or RAM). For example, application 622 may also be stored in removable storage media 610, read-only memory 608, and/or mass storage device 612.

Those skilled in the art will understand that the computer system 600 can include other processes and/or software and hardware components, such as an operating system that controls allocation and use of hardware resources.

As discussed herein, embodiments of the present invention include various steps or operations. A variety of these steps may be performed by hardware components or may be embodied in machine-executable instructions, which may be used to cause a general-purpose or special-purpose processor programmed with the instructions to perform the operations. Alternatively, the steps may be performed by a combination of hardware, software, and/or firmware. The term "module" refers to a self-contained functional component, which can include hardware, software, firmware, or any combination thereof.

One of ordinary skill in the art will readily appreciate and understand, upon reading this description, that embodiments of an apparatus may include a computer/computing device operable to perform some (but not necessarily all) of the described process.

Embodiments of a computer-readable medium storing a program or data structure include a computer-readable medium storing a program that, when executed, can cause a processor to perform some (but not necessarily all) of the described process.

Where a process is described herein, those of ordinary skill in the art will appreciate that the process may operate without any user intervention. In another embodiment, the process includes some human intervention (e.g., a step is performed by or with the assistance of a human).

As used in this description, the term "portion" means some or all. So, for example, "A portion of X" may include some of "X" or all of "X". In the context of a conversation, the term "portion" means some or all of the conversation.

As used herein, including in the claims, the phrase "at least some" means "one or more," and includes the case of only one. Thus, e.g., the phrase "at least some ABCs" means "one or more ABCs" and includes the case of only one ABC.

As used herein, including in the claims, the phrase "based on" means "based in part on" or "based, at least in part, on," and is not exclusive. Thus, e.g., the phrase "based on factor X" means "based in part on factor X" or "based, at least in part, on factor X." Unless specifically stated by use of the word "only", the phrase "based on X" does not mean "based only on X."

As used herein, including in the claims, the phrase "using" means "using at least," and is not exclusive. Thus, e.g., the phrase "using X" means "using at least X." Unless specifically stated by use of the word "only", the phrase "using X" does not mean "using only X."

In general, as used herein, including in the claims, unless the word "only" is specifically used in a phrase, it should not be read into that phrase.

As used herein, including in the claims, the phrase "distinct" means "at least partially distinct." Unless specifically stated, distinct does not mean fully distinct. Thus, e.g., the phrase, "X is distinct from Y" means that "X is at least partially distinct from Y," and does not mean that "X is fully distinct from Y." Thus, as used herein, including in the claims, the phrase "X is distinct from Y" means that X differs from Y in at least some way.

As used herein, including in the claims, a list may include only one item, and, unless otherwise stated, a list of multiple items need not be ordered in any particular manner. A list may include duplicate items. For example, as used herein, the phrase "a list of XYZs" may include one or more "XYZs".

It should be appreciated that the words "first" and "second" in the description and claims are used to distinguish or identify, and not to show a serial or numerical limitation. Similarly, the use of letter or numerical labels (such as "(a)", "(b)", and the like) are used to help distinguish and/or identify, and not to show any serial or numerical limitation or ordering.

No ordering is implied by any of the labeled boxes in any of the flow diagrams unless specifically shown and stated. When disconnected boxes are shown in a diagram, the activities associated with those boxes may be performed in any order, including fully or partially in parallel.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

The invention claimed is:

1. A method for evaluating growing media, the method comprising:
   (A) receiving from a third party at least one third party product list;
   (B) providing a first growing media test kit to a user, the first growing media test kit including a growing media testing device;
   (C) instructing the user to provide a first sample of growing media;
   (D) evaluating the first sample of growing media to determine a first nutrient level of at least one nutrient and/or a first pH level;
   (E) providing to the user results based at least in part on the evaluation in (D);
   (F) providing to the user at least one product recommendation based at least in part on the evaluation in (D), the at least one product recommendation chosen from the at least one third party product list.

2. The method of claim 1 wherein the providing to the user at least one product recommendation in (F) includes providing a link to at least one recommended product.

3. The method of claim 2 wherein the link includes an affiliate link to the at least one recommended product.

4. The method of claim 1 wherein the at least one product recommendation includes a growing media amendment, a plant, a plant seed, a plant seedling, a plant pot, and soil.

5. The method of claim 1 wherein the growing media testing device includes at least one of an ion-exchange resin, an N-P-K test meter, a color metric strip, litmus paper, an LED color variation test device, a pH meter, a Mehlich-3 test device, a Bray test device, an Olsen test device, and saturated paste.

6. The method of claim 1 wherein instructing the user to provide a first sample of growing media further comprises providing guidance to the user regarding locating and/or collecting the sample of growing media.

7. The method of claim 6 wherein the guidance provided to the user includes guidance regarding at least one of: measuring a volume of a growing area, determining a quantity of growing media samples to collect given a volume of growing area, determining a depth at which a growing media sample is taken, and collecting growing media samples from a growing area.

8. The method of claim 1 wherein the providing the results in (E) includes providing the results via a mobile application.

9. The method of claim 1 wherein the providing the at least one product recommendation in (F) includes providing the at least one product recommendation via a mobile application.

10. The method of claim 1 wherein the at least one nutrient includes at least one of nitrogen, phosphorus, potassium, sulfur, calcium, magnesium, sodium, iron, manganese, boron, copper, zinc, and aluminum.

11. A method for evaluating growing media, the method comprising:
   (A) receiving from a third party at least one customization element selected from the group: a logo, contact information, and a color scheme;

(B) providing a first growing media test kit to a user, the first growing media test kit including a first growing media testing device;
(C) instructing the user to provide a first sample of growing media;
(D) evaluating the first sample of growing media to determine a first nutrient level of at least one nutrient and/or a first pH level;
(E) providing to the user results based at least in part on the evaluation in (D); and
(F) providing to the user at least one product recommendation based at least in part on the evaluation in (D);
wherein the providing to the user results in (E) includes providing a report including the at least one customization element.

12. The method of claim 11 wherein the providing to the user at least one recommendation in (F) includes providing a link to at least one recommended product.

13. The method of claim 12 wherein the link includes an affiliate link to the at least one recommended product.

14. The method of claim 12 wherein the at least one recommended product includes a growing media amendment, a plant, a plant seed, a plant seedling, a plant pot, and soil.

15. The method of claim 11 wherein the growing media testing device includes at least one of an ion-exchange resin, an N-P-K test meter, a color metric strip, litmus paper, an LED color variation test device, a pH meter, a Mehlich-3 test device, a Bray test device, an Olsen test device, and saturated paste.

16. The method of claim 11 wherein instructing the user to provide a first sample of growing media further comprises providing guidance to the user regarding locating and/or collecting the sample of growing media.

17. The method of claim 16 wherein the guidance provided to the user includes guidance regarding at least one of: measuring a volume of a growing area, determining a quantity of growing media samples to collect given a volume of growing area, determining a depth at which a growing media sample is taken, and collecting growing media samples from a growing area.

18. The method of claim 11 wherein the providing the results in (E) includes providing the results via a mobile application.

19. The method of claim 11 wherein the providing the at least one product recommendation in (F) includes providing the at least one product recommendation via a mobile application.

20. The method of claim 11 wherein the at least one nutrient includes at least one of nitrogen, phosphorus, potassium, sulfur, calcium, magnesium, sodium, iron, manganese, boron, copper, zinc, and aluminum.

* * * * *